United States Patent [19]

Pastorino et al.

[11] 4,443,376
[45] Apr. 17, 1984

[54] GEM-DIPEROXYESTERS

[75] Inventors: Ronald L. Pastorino, Larkspur; Lawrence A. Bock, Walnut Creek; Reidar Halle, Novato, all of Calif.

[73] Assignee: Argus Chemical Corporation, Brooklyn, N.Y.

[21] Appl. No.: 424,820

[22] Filed: Sep. 27, 1982

Related U.S. Application Data

[62] Division of Ser. No. 166,210, Jul. 7, 1980, Pat. No. 4,370,459.

[51] Int. Cl.$^3$ .......................................... C07C 179/14
[52] U.S. Cl. ............................................. 260/453 RZ
[58] Field of Search ................................. 260/453 RZ

[56] References Cited

U.S. PATENT DOCUMENTS 3,652,631  3/1972  Stevens ..................... 260/453 RZ Primary Examiner—John M. Ford
Assistant Examiner—Robert C. Whittenbaugh
Attorney, Agent, or Firm—Townsend and Townsend

[57] ABSTRACT

Gem-diperoxyesters of the formula:

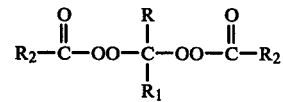

where R is selected from methyl and ethyl; $R_1$ is ethyl when R is ethyl; $R_1$ is hydroxyalkyl of 1 to 7 carbon atoms when R is methyl; and each $R_2$ is

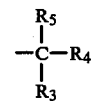

where each of $R_3$, $R_4$, and $R_5$ is selected from hydrogen and alkyl, provided not more than one of $R_3$, $R_4$, and $R_5$ is hydrogen, $R_3$, $R_4$, and $R_5$ collectively containing from 2 to 12 carbon atoms.

The compounds are particularly efficient at varying temperatures from ambient to 60° C. for the initiation of the polymerization of vinyl chloride. They also have high efficiency in the curing of polyester resins and in the polymerization of other monomers and comonomers having ethylenic unsaturation.

8 Claims, No Drawings

GEM-DIPEROXYESTERS

This is a division of application Ser. No. 166,210, filed July 7, 1980, now U.S. Pat. No. 4,370,459.

This invention relates to novel gem-diperoxyesters and their use as polymerization initiators for monomers and comonomers having ethylenic unsaturation, such as vinyl chloride, and for curing polyester resins.

Japanese Pat. Nos. 49(1974)-2993, 49(1974)-48928 and 50(1975)-23079 disclose the reaction of certain ketone peroxides and acid chlorides to form peroxyesters of the formula:

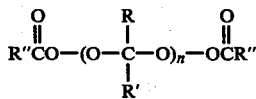

where R, R' are alkyl radicals of from 1-4 carbons, R' is alkyl, aralkyl, alkoxy of from 1-12 carbons, and n is 1-6.

The present invention provides a group of related molecules, some of which fall within the broad generic disclosures of the Japanese patents but which are surprisingly more efficient than the molecules actually described in the Japanese patents.

More particularly, the present invention provides gem-peroxyesters of the formula:

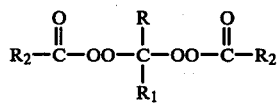

where R is selected from methyl and ethyl; $R_1$ is ethyl when R is ethyl; $R_1$ is hydroxyalkyl of 1 to 7 carbon atoms when R is methyl; and each $R_2$ is

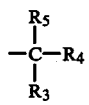

where each of $R_3$, $R_4$, and $R_5$ is selected from hydrogen and alkyl, provided not more than one of $R_3$, $R_4$, and $R_5$ is hydrogen, $R_3$, $R_4$, and $R_5$ collectively containing from 2 to 12 carbon atoms.

Preferred materials within the above general formula are those wherein R and $R_1$ are ethyl and wherein $R_2$ is 3-heptyl or 3-pentyl. However, in general $R_2$ may be any alkyl group which is bonded to its adjacent carbonyl group through a secondary or tertiary carbon atom. As noted, R may be methyl, in which case $R_1$ is hydroxyalkyl. In the preferred embodiment when R is methyl, $R_1$ is 2-methyl-2-hydroxypropyl.

The new peroxides are prepared by reacting the corresponding acid chloride with the corresponding ketone hydroperoxide monomer in accordance with the following equation, with R, $R_1$, and $R_2$ having the above stated definitions:

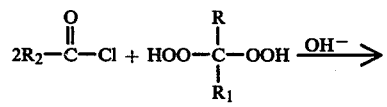

-continued

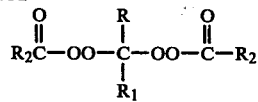

The predominant and desired end product is the 2:1 adduct shown in the above equation. One major peroxide by-product obtained in this reaction, which varies in amount depending upon the reactants and conditions, is the 1:1 adduct (R, $R_1$, and $R_2$ again have the above stated definitions):

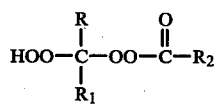

If desired, in certain instances where other products such as the 1:1 adduct are obtained, the 2:1 adduct could be separated by silica gel chromatography and utilized in the pure form. However, with a number of our novel gem-diperoxyesters separation is generally not practical because of their lower thermal stability and, in those cases where a mixture of adducts was obtained in the synthesis, the mixture was used directly as a polymerization initiator or as a polyester curing catalyst.

Example 1 is a typical synthesis for the ketone hydroperoxide monomers utilized for preparing the present compounds.

EXAMPLE 1

Diethylketone Hydroperoxide Monomer (DEKHP)

In a 125 ml round bottom flask equipped with a magnetic stirring bar is placed 28.56 g (0.42 mole) of 50% hydrogen peroxide. This is cooled to about 10° C. with an ice bath and two drops (ca. 0.08 g) of 78% sulfuric acid is added. Then 17.2 g (0.20 moles) of diethyl ketone is slowly added. The rate of addition is controlled to keep the temperature below 12° C. After completion of the addition, the ice bath is removed and the hazy mixture is stirred at room temperature for two hours.

The reaction solution is worked up by pouring it onto a saturated sodium chloride solution and adding a small amount of ether to aid in phase separation. The aqueous layer is removed and the organic phase is washed once with aqueous sodium chloride solution, twice with aqueous sodium bicarbonate, and twice with aqueous sodium chloride solution. The organic layer is dried with sodium sulfate and then the volatiles are removed on a vacuum pump to leave a product weighing 15.3 grams.

Product Active Oxygen (A.O.) Analysis: theory, 23.53; found, 18.61; 79.09% pure; 44.5% weight yield.

Liquid Chromatographic (L.C.) Analysis: (Bondapack C18 column, 80% $CH_3CN$/20% $H_2O$): 3.94 minutes, 78.4% (monomer); 4.40 minutes, 12.3% diethyl ketone (DEK); 5.43 minutes, 7.8% (dimer/oligomer); and three unknown peaks, 1.5% total.

It has been observed in numerous preparations that after the product has been stored in the refrigerator for several days, a solid would separate leaving a supernatant liquid phase. L.C. analysis of the solid showed it to be 98% monomer.

Synthesis of the other ketone peroxide monomers utilized for making the present compounds generally follows the above procedure. Specific molar ratios used for synthesis of the ketone peroxide monomers are shown below:

| Product | Mole Ratios | | |
|---|---|---|---|
| | Ketone | $H_2O_2$ | $H_2SO_4$ |
| 1. Diethylketone Hydroperoxide (DEKHP) | 1.0 | 2.1 | .003 |
| 2. Methyl Ethyl Ketone Hydroperoxide (MEKHP) | 1.0 | 3.8 | none |
| 3. Diacetone Alcohol Hydroperoxide (DAAHP) | 1.0 | 2.1 | .005 |

The gem-peroxyesters of this invention are prepared by reacting a suitable acid halide with the ketone peroxide monomer. The following example is a typical synthesis is which 2,2-bis(2-ethyl hexanoylperoxy)butane is prepared. This compound is included with those compositions disclosed in the above referenced Japanese patents and is selected herein for reference purposes.

EXAMPLE 2

2,2-Bis(2-Ethyl Hexanoylperoxy)Butane (KP-A)

In a 250 ml round bottom flask equipped with a stirring motor and thermometer is placed 25.82 g of potassium hydroxide pellets (0.40 mole, 86.9% pure) and 35.2 g of water (2.14 total moles of water added, including the water contained in KOH pellets). The solution is cooled to about 5° C. and then 33.62 g (0.192 mole, 69.68% pure) of methyl ethyl ketone hydroperoxide monomer is added slowly. A solid forms and stirring is difficult. Petroleum ether is added to aid the stirring. Following completion of the monomer addition, the solution is cooled to about 0° C., and 25.98 g (0.16 mole) of 2-ethyl hexanoyl chloride is slowly added. Care must be taken to prevent excessive temperature rise during acid chloride addition. After completion of the acid chloride addition, the reaction temperature is allowed to slowly rise to about +7° C. and stirring is maintained for 2½ hours.

The entire work-up procedure is conducted using solutions cooled to about 5° C. to prevent decomposition of the peroxyester product. The reaction solution is diluted with cold water and transferred to a pre-cooled separatory funnel with the aid of cold ether. The aqueous phase is removed, and the organic layer is washed three times with cold 5% potassium hydroxide solution and three times with cold water. During the time period following the shaking of the separatory funnel while the phases are separating, the separatory funnel is placed in an ice water-filled beaker to keep the temperature as low as possible. The organic phase is dried with sodium sulfate and then the volatiles are removed on a vacuum pump at low temperature to leave a product weighing 29.9 grams.

Product A.O. Analysis: theory, 8.56; found, 6.78; 79.21% pure; 79.2% weight yield.

Infrared Analysis: carbonyl band at 1780 cm$^{-1}$.

HPLC Analysis ($\mu$CN column, hexane solvent): DEK, 6.2 area percent; 2:1 adduct, 73.0%; other components, 20.8%.

Utilizing a similar procedure, one of the novel compounds of this invention, 3,3-bis(2-ethyl butanoylperoxy)pentane, was prepared by the following steps.

EXAMPLE 3

3,3-Bis(2-Ethyl Butanoylperoxy)Pentane (KP-F)

In a 250 ml round bottom flask equipped with a stirring motor and thermometer is placed 12.17 g of potassium hydroxide pellets (0.1875 moles 86.4% pure) and 16.3 g of water (0.997 total moles of water added, including the water contained in the KOH pellets). The solution is cooled to about 5° C. and then 17.42 g (0.075 moles, 58.55% pure) of diethyl ketone hydroperoxide monomer is added slowly. A solid forms and stirring is difficult. Petroleum ether (25 ml) is added to aid the stirring. Following completion of the monomer addition, the solution is cooled to about 0° C. and 19.67 g (0.1463 moles) of 2-ethyl butanoyl chloride is slowly added. Care must be taken to prevent excessive temperature rise during acid chloride addition. After completion of the acid chloride addition, the reaction temperature is allowed to slowly rise to about +5° C. and stirring is maintained for 1½ hours.

The entire work-up procedure is conducted exactly as outlined in Example 2 above to leave a product weighing 22.64 grams.

Product A.O. Analysis: theory 9.64; found 7.91; 82.05% pure; 76.5% weight yield.

Infrared Analysis: carbonyl band at 1770 cm$^{-1}$.

HPLC Analysis ($\mu$CN column, hexane solvent): DEK, 7.7 area percent; 2:1 adduct, 81.8%; other components, 10.5%.

All of the compositions set forth in Table I below were prepared by similar procedures by substituting the appropriate ketone peroxide monomer and acid chloride. It should be noted that the mole ratio of acid chloride to hydroperoxide monomer is theoretically 2:1. However, in practice as shown in above Examples 2 and 3, the mole ratio of acid chloride to hydroperoxide may be varied from less than 1:1 to 2:1 while still providing the desired 2:1 adduct. The amounts employed for the compounds of Table I are as follows:

| Peroxyester | Acid Chloride | Ketone Peroxide |
|---|---|---|
| KP-A | 0.16 | 0.192 |
| KP-B | 0.18 | 0.216 |
| KP-C | 0.224[1] | 0.27 |
| KP-D | 0.1125 | 0.075 |
| KP-E | 0.08 | 0.096 |
| KP-F | 0.1463 | 0.075 |
| KP-G[2] | 0.08 | 0.05 |
| KP-H[2] | 0.08 | 0.05 |

[1]Reactant was an isomeric mixture as described in U.S. Pat. No. 3,624,123.
[2]Pyridine as catalyst instead of KOH.

TABLE 1

| Gem-Diperoxyester | Code Letter | Mol. Wt. | T.A.O. | % A.O. Found | % Purity | Yield Wt. Yld. (g)/ Theor. Yld. (g) | % Wt. Yield | HPLC Anal. (Area %) | |
|---|---|---|---|---|---|---|---|---|---|
| 2,2-bis(2-ethyl hexanoylperoxy) butane | KP-A | 374 | 8.56 | 6.78 | 79.21 | 29.9/29.9 | 79.2 | DEK 2:1 Other | 6.2 73.0 20.8 |
| 3,3-bis(pivaloyl-peroxy)pentane | KP-B | 304 | 10.53 | 8.91 | 84.62 | 8.7/12.15 | 60.6 | Not Done | |
| 3,3-bis(neo-decanoylperoxy) | KP-C | 444 | 7.21 | 4.86 | 67.41 | 12.3/17.8 | 46.6 | DEK 2:1 | 43.3 31.0 |

TABLE 1-continued

| Gem-Diperoxyester | Code Letter | Mol. Wt. | T.A.O. | % A.O. Found | % Purity | Yield Wt. Yld. (g)/ Theor. Yld. (g) | % Wt. Yield | HPLC Anal. (Area %) | |
|---|---|---|---|---|---|---|---|---|---|
| pentane 3,3-bis(2-ethyl hexanoylperoxy) pentane | KP-D | 388 | 8.25 | 6.18 | 74.94 | 20.0/21.82 | 68.7 | Other DEK 2:1 1:1 | 25.7 27.9 45.1 11.1 |
| 3,3-bis(2-methyl propionylperoxy) pentane | KP-E | 276 | 11.59 | 8.71 | 75.15 | 13.0/11.0 | 88.5 | Other DEK 2:1 1:1 | 15.9 29.2 61.9 4.2 |
| 3,3-bis(2-ethyl butanoylperoxy) pentane | KP-F | 332 | 9.64 | 7.91 | 82.05 | 22.64/24.28 | 76.5 | Other DEK 2:1 | 4.7 7.7 81.8 |
| 3,3-bis(2-methyl pentanoylperoxy) pentane | KP-G | 332 | 9.64 | 7.47 | 77.49 | 12.4/13.5 | 71.2 | Other DEK 2:1 Other | 10.5 24.3 72.1 3.6 |
| 2,2-bis(2-ethyl hexanoylperoxy)- 4-hydroxy-4- methylpentane | KP-H | 418 | 7.65 | 5.93 | 77.52 | 5.2/10.0 | 40.2 | Not Done | |
| 2,2-bis(2-ethyl butanoylperoxy)- 4-hydroxy-4- methylpentane | KP-I | 362 | 8.84 | 5.65 | 63.91 | 5.5/14.5 | 24.2 | Not Done | |

Half lifes of certain gem-diperoxyesters of Table I were determined as shown in Table II below:

TABLE II

HALF-LIFES OF VARIOUS GEM-DIPEROXYESTERS

| Gem-Diperoxyester | 10 Hour Half-Life Temperature, °C.[1] |
|---|---|
| 1. KP-A | 43.7 |
| 2. KP-B | 24 |
| 3. KP-C | 23.3 |
| 4. KP-D | 39.7 |
| 5. KP-F | 40 |

[1] 0.2 M in benzene.

The new compounds of this invention have utility as polymerization initiators for monomers and comonomers having ethylenic unsaturation. Preferably, the monomer polymerized will be selected from vinyl chloride, ethylene, styrene and methyl methacrylate, and the comonomers will preferably be vinyl chloride and vinyl acetate. Use of the present compositions for the polymerization of such systems provides the advantages of permitting effective conversion of monomer to polymer at relatively low temperature.

POLYVINYL CHLORIDE

A series of polymerizations was performed to illustrate the improved efficiencies of the new compounds as initiators of vinyl chloride monomer. 2,2-Bis(2-ethyl hexanoylperoxy)butane (KP-A) is one compound that can be made by the procedures of the above referenced Japanese patents and was included as typical of the prior art.

The data in Table III were obtained in the following manner:

The suspension polymerization were performed in pop bottles using uninhibited monomer. Duplicate bottles were analyzed at each polymerization time interval. The following table lists some general information about the polymerization procedure used.

| Polymerization Temperature, °C. | Bottle Size fl. oz. | Mixing Speed, RPM | H2O/ VCM Ratio | Amt. Suspension Agent/100 g. VCM |
|---|---|---|---|---|
| 22, 40, and 50 | 6.5 | 25 | 1.88 | 0.23 g. Dow Methocel 65HG, 50 cps |
| 55 and 60 | 12 | 42 | 2.5 | 0.35 g. Dow Methocel 90HG, 100 cps |

After the desired amounts of reactants were added to the pop bottles, they were capped, the contents almost melted, and the bottles placed in a rotating constant temperature bath at the temperatures and for the times shown in Table III. The bottles were frozen before venting-off excess monomer. The polymer was filtered, washed, and dried. All initiator concentrations shown have been corrected for purity.

TABLE III

COMPARISON OF VARIOUS DIPEROXYESTERS AS INITIATORS OF VINYL CHLORIDE

| Gem-Diperoxyester Code Letter (See TABLE I) | % Wt. Used | Moles ($\times 10^{-4}$) Initiator/100g VCM | % Conversion |
|---|---|---|---|
| SET 1–7 hrs. at 22° C. | | | |
| 1. KP-A | 0.20 | 5.35 | 5.0 |
| 2. KP-B | 0.10 | 3.29 | 52.2 |
| 3. KP-C | 0.10 | 2.25 | 27.8 |
| 4. KP-D | 0.20 | 5.15 | 10.7 |
| 5. KP-E | 0.20 | 7.25 | 0.5 |
| 6. KP-F | 0.20 | 6.02 | 4.3 |
| 7. KP-G | 0.20 | 6.02 | 1.6 |
| SET 2–7 hrs. at 40° C. | | | |
| 1. KP-A | 0.15 | 4.01 | 45.9 |
| 2. KP-B | 0.122 | 4.01 | 90.4 |
| 3. KP-C | 0.178 | 4.01 | 63.1 |
| 4. KP-D | 0.155 | 4.01 | 75.4 |
| 5. KP-E | 0.111 | 4.01 | 39.6 |
| 6. KP-F | 0.133 | 4.01 | 88.3 |
| 7. KP-G | 0.133 | 4.01 | 67.3 |
| SET 3–6 hrs. at 50° C. | | | |
| 1. KP-A | 0.094 | 2.50 | 75.85 |
| 2. KP-B | 0.076 | 2.50 | 51.8 |
| 3. KP-C | 0.111 | 2.50 | 38.0 |
| 4. KP-D | 0.058 | 1.50 | 79.1 |
| | 0.097 | 2.50 | 89.1 |
| 5. KP-E | 0.069 | 2.50 | 74.4 |

TABLE III-continued
COMPARISON OF VARIOUS DIPEROXYESTERS AS INITIATORS OF VINYL CHLORIDE

| Gem-Diperoxyester Code Letter (See TABLE I) | % Wt. Used | Moles (× 10⁻⁴) Initiator/100g VCM | % Conversion |
|---|---|---|---|
| 6. KP-F | 0.056 | 1.50 | 82.5 |
|  | 0.083 | 2.50 | 92.5 |
| 7. KP-G | 0.083 | 2.50 | 88.5 |
| SET 4–5.5 hrs. at 55° C. | | | |
| 1. KP-A | 0.047 | 1.25 | 53.4 |
|  | 0.065 | 1.75 | 72.1 |
| 2. KP-D | 0.049 | 1.25 | 69.6 |
|  | 0.068 | 1.75 | 84.2 |
| 3. KP-E | 0.048 | 1.75 | 76.1 |
| 4. KP-F | 0.042 | 1.25 | 74.1 |
|  | 0.058 | 1.75 | 85.9 |
| 5. KP-G | 0.042 | 1.25 | 72.8 |
|  | 0.058 | 1.75 | 86.2 |
| 6. KP-H | 0.073 | 1.75 | 63.9 |
| 7. KP-I | 0.063 | 1.75 | 66.1 |
| SET 5–5 hrs. at 60° C. | | | |
| 1. KP-A | 0.047 | 1.25 | 67.8 |
|  | 0.065 | 1.75 | 83.2 |
| 2. KP-D | 0.049 | 1.25 | 70.5 |
|  | 0.068 | 1.75 | 83.8 |
| 3. KP-E | 0.035 | 1.25 | 71.5 |
|  | 0.048 | 1.75 | 86.7 |
| 4. KP-F | 0.042 | 1.25 | 67.8 |
|  | 0.058 | 1.75 | 81.8 |
| 5. KP-G | 0.042 | 1.25 | 72.6 |
|  | 0.058 | 1.75 | 85.9 |
| 6. KP-H | 0.073 | 1.75 | 58.1 |
| 7. KP-I | 0.063 | 1.75 | 65.4 |

POLYESTER-RESINS

The unsaturated polyester resins cured by the present process comprise those polyesters described in U.S. Pat. No. 4,129,613, the disclosure thereof being incorporated by reference herein. The following Table IV is typical of the improved results obtained with the present compounds.

TABLE IV
HOT BLOCK GEL TESTS WITH POLYESTER RESIN USING VARIOUS GEM-DIPEROXYESTERS

Resin: USS Chemical MR-941 (Isophthalic)
Block Temp.: 180 ± 1° F. (82° C.)
Peroxide Concentration Corrected for Purity, Except for DBCPD¹

| Peroxide | % Wt Used | Moles Peroxide (× 10⁻³)/100 g Resin | Gel Time, Min. | Exotherm Time, Min. | Peak Temp, °F. |
|---|---|---|---|---|---|
| SET 1 | | | | | |
| 1. KP-B | 0.75 | 2.47 | 1'14" | 2'32" | 221 |
| 2. KP-C | 0.75 | 1.69 | 1'25" | 2'47" | 225 |
| 3. KP-D | 0.75 | 1.93 | 1'48" | 2'29" | 249 |
| 4. DBCPD | 0.75 | — | 2'40" | 3'32" | 244 |
| SET 2 | | | | | |
| 1. KP-A | 0.75 | 2.01 | 2'12" | 2'53" | 275 |
| 2. KP-D | 0.75 | 1.93 | 1'55" | 2'42" | 260 |
| 3. KP-F | 0.75 | 2.26 | 1'49" | 2'30" | 271 |
| 4. DBCPD | 0.75 | — | 2'53" | 3'46" | 260 |

¹Di-4-t-butyl cyclohexylperoxydicarbonate

Apart from the employment of the novel compounds of this invention, the polymerization and curing processes in which they are used are consistent with the teachings of the prior art, including quantities of reactants, temperatures, solvents, optional additives and the like.

We claim:

1. An organic peroxide of the formula:

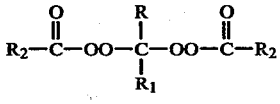

where R is selected from methyl and ethyl; $R_1$ is ethyl when R is ethyl; $R_1$ is hydroxyalkyl of 1 to 7 carbon atoms when R is methyl; and each $R_2$ is

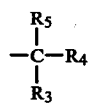

where each of $R_3$, $R_4$, and $R_5$ is selected from hydrogen and alkyl, provided not more than one of $R_3$, $R_4$, and $R_5$ is hydrogen, and $R_3$, $R_4$, and $R_5$ collectively containing from 2 to 12 carbon atoms.

2. An organic peroxide in accordance with claim 1 wherein R and $R_1$ are ethyl.

3. An organic peroxide in accordance with claim 1 wherein R is methyl and $R_1$ is 2-methyl-2-hydroxypropyl.

4. An organic peroxide in accordance with claim 1 wherein each $R_2$ is bonded to its carbonyl group through a secondary carbon atom.

5. An organic peroxide in accordance with claim 2 wherein $R_2$ is selected from 3-heptyl, 2-methyl-2-propyl, 2-propyl, 3-pentyl, 2-pentyl, and t-nonyl.

6. An organic peroxide in accordance with claim 3 wherein $R_2$ is selected from 3-heptyl and 3-pentyl.

7. An organic peroxide in accordance with claim 2 wherein each $R_2$ is 3-heptyl.

8. An organic peroxide in accordance with claim 2 wherein each $R_2$ is 3-pentyl.

* * * * *